US010256220B2

(12) United States Patent
O'Brien et al.

(10) Patent No.: US 10,256,220 B2
(45) Date of Patent: Apr. 9, 2019

(54) OPTICAL SENSOR

(71) Applicant: OSRAM Opto Semiconductors GmbH, Regensburg (DE)

(72) Inventors: David O'Brien, Portland, OR (US); Tim Böscke, Regensburg (DE); Sebastian Pielnhofer, Berg (DE)

(73) Assignee: OSRAM Opto Semiconductors GmbH (DE)

( * ) Notice: Subject to any disclaimer, the term of this patent is extended or adjusted under 35 U.S.C. 154(b) by 0 days.

(21) Appl. No.: 15/769,423

(22) PCT Filed: Oct. 21, 2016

(86) PCT No.: PCT/EP2016/075429
§ 371 (c)(1),
(2) Date: Apr. 19, 2018

(87) PCT Pub. No.: WO2017/068148
PCT Pub. Date: Apr. 27, 2017

(65) Prior Publication Data
US 2018/0303359 A1 Oct. 25, 2018

(30) Foreign Application Priority Data
Oct. 21, 2015 (DE) .................. 10 2015 117 940

(51) Int. Cl.
*H01L 25/16* (2006.01)
*H01L 33/50* (2010.01)
(Continued)

(52) U.S. Cl.
CPC ........ *H01L 25/167* (2013.01); *A61B 5/02427* (2013.01); *A61B 5/02444* (2013.01);
(Continued)

(58) Field of Classification Search
CPC . H01L 25/042; H01L 25/075; H01L 25/0753; H01L 31/12; H01L 31/16;
(Continued)

(56) References Cited

U.S. PATENT DOCUMENTS

| 6,134,460 | A  | 10/2000 | Chance |
| 2004/0259363 | A1 | 12/2004 | Bawendi et al. |

(Continued)

FOREIGN PATENT DOCUMENTS

| DE | 10 2008 022 920 B4 | 5/2010 |
| EP | 2 074 658 B1 | 7/2009 |
| WO | 2014/092932 A1 | 6/2014 |

*Primary Examiner* — Scott B Geyer
(74) *Attorney, Agent, or Firm* — DLA Piper LLP (US)

(57) ABSTRACT

An optical sensor that captures a heart rate and/or a blood oxygen content includes a light source including a light emitter that emits electromagnetic radiation with a first wavelength range including green light, a second wavelength range including red light and a third wavelength range including infrared radiation, and three light detectors, each including a filter for electromagnetic radiation, wherein a first filter is transmissive for light of the first wavelength range and non-transmissive for light of the second wavelength range and the infrared radiation of the third wavelength range, a second filter is transmissive for light of the second wavelength range and non-transmissive for light of the first wavelength range and the infrared radiation of the third wavelength range and a third filter is transmissive for the infrared radiation of the third wavelength range and non-transmissive for light of the first and the second wavelength range.

14 Claims, 4 Drawing Sheets

(51) Int. Cl.
| | |
|---|---|
| H01L 31/0216 | (2014.01) |
| A61B 5/024 | (2006.01) |
| A61B 5/1455 | (2006.01) |
| H01L 25/04 | (2014.01) |
| H01L 25/075 | (2006.01) |
| H01L 31/0232 | (2014.01) |
| H01L 31/16 | (2006.01) |
| H01L 33/06 | (2010.01) |

(52) U.S. Cl.
CPC ........ A61B 5/14552 (2013.01); H01L 25/042 (2013.01); H01L 25/0753 (2013.01); H01L 31/02165 (2013.01); H01L 31/02327 (2013.01); H01L 31/16 (2013.01); H01L 33/06 (2013.01); H01L 33/50 (2013.01)

(58) Field of Classification Search
CPC .. H01L 31/02165; H01L 33/50–33/508; H01L 25/167; A61B 5/145; A61B 5/1455; A61B 5/14551; A61B 5/14552; A61B 5/02444; A61B 5/02427
See application file for complete search history.

(56) References Cited

U.S. PATENT DOCUMENTS

| | | |
|---|---|---|
| 2008/0291455 A1 | 11/2008 | Holland |
| 2009/0054752 A1 | 2/2009 | Jonnalagadda et al. |
| 2010/0049017 A1 | 2/2010 | LeBoeuf et al. |
| 2013/0313595 A1 | 11/2013 | Naasani et al. |
| 2014/0001494 A1* | 1/2014 | Shen ................ H01L 33/08 257/84 |
| 2015/0051498 A1 | 2/2015 | Darty |
| 2015/0133753 A1* | 5/2015 | Karp .................. A61B 5/6826 600/323 |
| 2015/0148633 A1 | 5/2015 | Park |
| 2015/0190063 A1 | 7/2015 | Zakharov et al. |
| 2015/0192714 A1 | 7/2015 | Jain |

* cited by examiner

OPTICAL SENSOR

TECHNICAL FIELD

This disclosure relates to an optical sensor that captures a heart rate and/or a blood oxygen content.

BACKGROUND

Optical sensors that capture a heart rate and/or a blood oxygen content can be realized by virtue of radiating the light from a light-emitting diode onto the skin. In so doing, the light is scattered by tissue below the skin and the intensity of the scattered light can be measured using a photodetector. Some of the radiated-in light is absorbed by hemoglobin molecules in the blood. Blood is pumped through the arteries driven by the heart, with the amount of blood in an artery not being constant, but pulsing with the same frequency as the heart rate. As a result, the amount of blood in the artery varies with the heart rate and the amount of available hemoglobin likewise varies. More of the light of the light-emitting diode, or less, is absorbed by the hemoglobin, depending on whether much or little hemoglobin is in the artery. As a result, the intensity of the scattered light also varies with the heart rate. This changing intensity can be detected by the photodetector. As a result, it is possible to deduce the heart rate from the change of the photocurrent of the photodetector. Such an optical heart rate sensor is known from DE 10 2008 022 920 B4.

There is nonetheless a need to provide an improved optical sensor that determines the heart rate, the sensor moreover being suitable to optionally determine a blood oxygen content.

SUMMARY

We provide an optical sensor that captures a heart rate and/or a blood oxygen content, including a light source including at least one light-emitting semiconductor chip and emits electromagnetic radiation with three different wavelength ranges, wherein a first wavelength range includes green light, a second wavelength range includes red light and a third wavelength range includes infrared radiation, and three light detectors, wherein the three light detectors each include a filter for electromagnetic radiation, wherein a first filter is transmissive for light of the first wavelength range and non-transmissive for light of the second wavelength range and the infrared radiation of the third wavelength range, a second filter is transmissive for light of the second wavelength range and non-transmissive for light of the first wavelength range and the infrared radiation of the third wavelength range and a third filter is transmissive for the infrared radiation of the third wavelength range and non-transmissive for light of the first and the second wavelength range, wherein the light-emitting semiconductor chip has an emission wavelength of less than 570 nanometers and the light source includes a conversion phosphor, the conversion phosphor converts the light of the semiconductor chip into electromagnetic radiation with the first wavelength range, the second wavelength range and the third wavelength range, the conversion phosphor comprises a matrix material with three different narrowband phosphors, and the emission wavelengths of the phosphors lie within the three wavelength ranges.

LIST OF REFERENCE SIGNS

Figure 1:
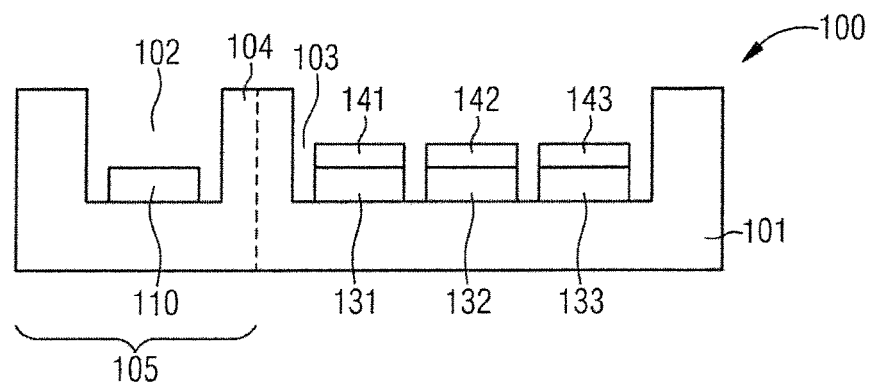
FIG. 1 schematically shows an optical sensor with a light source and three light detectors.

100 Optical sensor
101 Housing
102 First recess
103 Second recess
104 Web
105 Light source
110 Semiconductor chip
111 First semiconductor chip
112 Second semiconductor chip
113 Third semiconductor chip
120 Conversion phosphor
121 Protective layer
122 Glass plate
123 Spacer
131 First light detector
132 Second light detector
133 Third light detector
141 First filter
142 Second filter
143 Third filter
150 Electric circuit
151 Electric line
152 Electric line
153 Connector for a voltage supply
154 Controller for a semiconductor chip
155 Electric line
156 Evaluation electronics
157 Data line
158 Data interface
159 Data line

DETAILED DESCRIPTION

Our optical sensor that captures a heart rate and/or a blood oxygen content has a light source having at least one light-emitting semiconductor chip. The light source emits electromagnetic radiation with three different wavelength ranges, wherein a first wavelength range comprises green light, a second wavelength range comprises red light and a third wavelength range comprises infrared radiation. Moreover, the sensor has three light detectors, each having a filter for electromagnetic radiation. A first filter on a first light detector is transmissive for light of the first wavelength range and non-transmissive for light of the second wavelength range and infrared radiation of the third wavelength range. A second filter of the second light detector is transmissive for light of the second wavelength range and non-transmissive for light of the first wavelength range and infrared radiation of the third wavelength range. A third filter of a third light detector is transmissive for infrared radiation of the third wavelength range and non-transmissive for light of the first and the second wavelength range. The light-emitting semiconductor chip has an emission wavelength of less than 570 nanometers. The light source has a conversion phosphor, wherein the conversion phosphor converts the light of the semiconductor chip into electromagnetic radiation with the first wavelength range, the second wavelength range and the third wavelength range. The conversion phosphor has a matrix material with three different narrowband phosphors, wherein the emission wavelengths of the phosphors lie within the three wavelength ranges. "Narrowband" means that a full width at half maximum of an emission peak of the phosphor is less than 40 nanometers. Using the green light of the first wavelength range, it is possible to measure heart rate by the optical sensor. The red light of the second wavelength range and the infrared radiation of the third wavelength range are suitable for measuring the blood oxygen content using the optical sensor. By using three light detectors with three filters, each transmitting one of the three wavelength ranges and non-transmissive for the other two wavelength ranges, it is possible to carry out three measurements in the three wavelength ranges in parallel. It is advantageous to operate the light source in a pulsed fashion such that less energy is required than in continuous operation. By using the three light detectors with the three filters, it is possible to simultaneously carry out a measurement of both the heart rate and the blood oxygen content by one pulse from the light source.

The conversion phosphor having three narrowband phosphors in a matrix material is easy to produce and it facilitates a simple structure of the optical sensor. By using narrowband phosphors, use is made of the wavelengths suitable for measuring the heart rate and the blood oxygen content. In the process, as little light lying outside of the desired wavelength ranges as possible is created within the phosphor. Thus, the required light output of the light-emitting semiconductor chip can be reduced. This leads to power savings. Moreover, only a small component of the light not suitable for measuring the heart rate or the blood oxygen content is produced. Thus, the stray light component is reduced. Further, less light is radiated onto the skin, as a result of which less non-utilizable energy is transferred from the optical sensor onto the skin, leading to the optical sensor being more skin friendly.

The conversion phosphor may have quantum dots. Quantum dots are well suited to being a conversion phosphor since, first, they can easily be configured to absorb the light of the semiconductor chip. Moreover, they can be configured to emit light in a narrow wavelength range. In particular, by selecting quantum dots as conversion phosphors, it is possible to produce a light source having a narrowband emission of the light of the first and second wavelength range and the infrared radiation of the third wavelength range. In particular, it is possible to configure the light source such that the three wavelength ranges do not overlap.

To produce the light of the first wavelength range, use can be made of cadmium selenide or indium phosphide quantum dots with a first dimension of the quantum dots. The light of the second wavelength range can likewise be produced by cadmium selenide or indium phosphide quantum dots with a second dimension of the quantum dots, with the second dimension being larger than the first dimension. The infrared radiation of the third wavelength range can be produced by indium arsenide, lead selenide or copper indium phosphide quantum dots.

At least one filter may be an interference filter. Interference filters are filters consisting of layers with different refractive indices. By way of a suitable selection of the refractive indices and the layer thicknesses, it is possible in the process to produce a filter having a very narrowband transmission curve. By way of interference filters, it is possible, in particular, to provide filters for the light detectors that virtually completely transmit the electromagnetic radiation in one wavelength range and virtually completely suppress the electromagnetic radiation of the two other wavelength ranges.

The green light may have a wavelength of 530 to 610, the red light has a wavelength of 620 to 700 nanometers and the infrared radiation has a wavelength of greater than 800 nanometers. These three wavelength ranges are particularly well-suited to the use in an optical sensor, in particular to determine a heart rate and/or a blood oxygen content.

The materials explained below, for example, are possible for producing converted light within the aforementioned wavelengths by quantum dots. For the green light of the first wavelength range with a wavelength around 570 nanometers, use can be made here of cadmium selenide quantum dots with a diameter of 3.0 to 3.5. Alternatively, the use of indium phosphide quantum dots with a diameter of 1.8 to 2.2 nanometers is possible for the green light.

Cadmium selenide quantum dots with a diameter of 7.5 to 8.5 can be used for the red light of the second wavelength range with a wavelength around 660 nanometers. Alternatively, the use of indium phosphide quantum dots with a diameter of 2.8 to 3.2 nanometers is possible for the green light.

For the infrared radiation of the third wavelength range with a wavelength of greater than 800 nanometers, indium arsenide quantum dots with a diameter of 3.0 to 6.0 nanometers are possible. Alternatively, lead selenide quantum dots with a diameter of greater than 5.0 nanometers can be used for the infrared radiation of the third wavelength range with a wavelength of greater than 800 nanometers. A further alternative for the infrared radiation of the third wavelength range with a wavelength of greater than 800 nanometers is the use of copper indium phosphide quantum dots with a diameter of 2.5 to 5.8 nanometers.

The optical sensor may have an electronic circuit configured to evaluate signals from the light detectors and supply the light source with power. As a result, it is possible to produce an integrated component with small dimensions which only requires connectors to supply voltage and a data interface.

The power supply of the light source can be operated in a pulsed manner. The circuit used to evaluate the signals from the light detectors is configured to take account of the pulses. As a result of the pulsed operation of the light source, it is possible to produce an optical sensor having a lower energy consumption than an optical sensor in which the light source is operated continuously. By way of example, taking account of the pulses can be effectuated by virtue of filtering being carried out at a pulse frequency. As a result, the signal evaluation is improved.

The above-described properties, features and advantages and the manner in which they are achieved will become clearer and more easily understandable in conjunction with the following description of examples, explained in more detail in conjunction with the drawings.

FIG. 1 shows a cross section through an optical sensor 100. The optical sensor 100 has a housing 101. For example, the housing 101 can be an injection molded part made of a polymer. It is likewise possible for the housing 101 to consist of a different material. The housing 101 has a first recess 102 and a second recess 103. Between the two recesses 102, 103, there is a web 104 made of the material of the housing 101. Thus, the two recesses 102, 103 are separated from one another by the web 104. A semiconductor chip 110 is mounted in the first recess 102. The semiconductor chip 110 in the first recess 102 and the adjoining parts of the housing 101 form a light source 105. The light source 105 is configured to emit electromagnetic radiation with three different wavelength ranges. In particular, the semiconductor chip 110 is configured to emit the electromagnetic radiation with the three different wavelength ranges. A first wavelength range comprises green light, a second wavelength range comprises red light and a third wavelength range comprises infrared radiation. Three light detectors 131, 132, 133 are mounted in the second recess 103, with each light detector having a filter 141, 142, 143. The first filter 141 is mounted on the first light detector 131 and configured to transmit light of the first wavelength range and not to transmit light of the second and third wavelength range. The second filter 142 is mounted on the second light detector 132 and configured to transmit electromagnetic radiation of the second wavelength range and not to transmit electromagnetic radiation of the first and third wavelength range. The third filter 143 is mounted on third light detector 133 and configured to transmit electromagnetic radiation of the third wavelength range and not to transmit electromagnetic radiation of the first and second wavelength range.

To "transmit" means that at least 85%, preferably at least 90%, particularly preferably at least 95% and most particularly preferably at least 98% of the light of the considered wavelength range passes through the corresponding filter. "Not to transmit" means that at most 10%, preferably at most 5%, particularly preferably at most 2% and most particularly preferably at most 1% of the light of the considered wavelength range passes through the corresponding filter.

The optical sensor 100 is configured to be placed onto a body part or onto a surface of a human body part. The electromagnetic radiation of the light source 105 is reflected or scattered within a tissue of the body part. The scattered light can be detected by the three light detectors 131, 132, 133. The signal in the three light detectors 131, 132, 133 changes due to a heart rate and/or a blood oxygen content within the body part.

Figure 2:
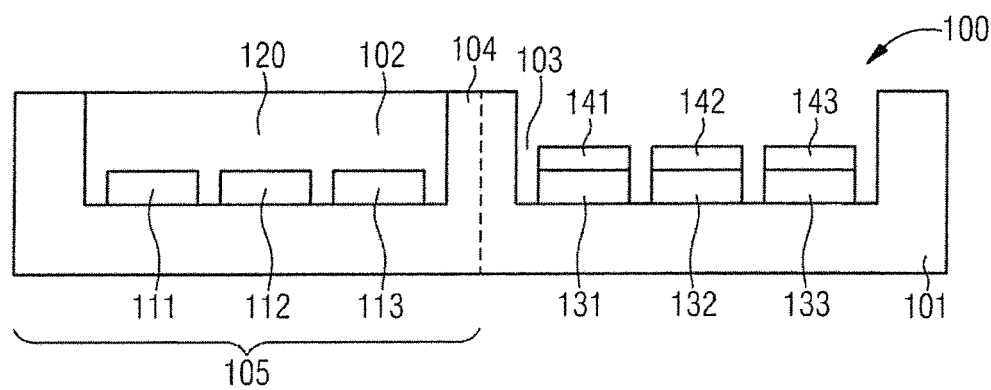
FIG. 2 schematically shows an optical sensor with three semiconductor chips, a conversion phosphor, and three light detectors.

FIG. 2 shows a cross section through a further optical sensor 100. The optical sensor 100 has a housing 101, a first recess 102, a second recess 103 and a web 104 between the two recesses 102, 103. Three light detectors 131, 132, 133 with associated filters 141, 142, 143 are arranged, in turn, in the second recess 103, like in FIG. 1. Three semiconductor chips 111, 112, 113 are arranged in the first recess 102. The first semiconductor chip 111 emits light with a first wavelength of less than 570 nanometers. A second semiconductor chip 112 emits red light; a third semiconductor chip 113 emits infrared radiation. The first recess 102 is filled with the conversion phosphor 120. This conversion phosphor converts the light of the first semiconductor chip into green light of the first wavelength range and it is transparent to the light of the second semiconductor chip 112 and the infrared radiation of the third semiconductor chip 113. The conversion phosphor 120 can consist of phosphor particles in a matrix material. However, other conversion phosphors are also possible. The three semiconductor chips 111, 112, 113, the conversion phosphor 120 and the adjoining parts of the housing 101 form the light source 105.

Figure 3:
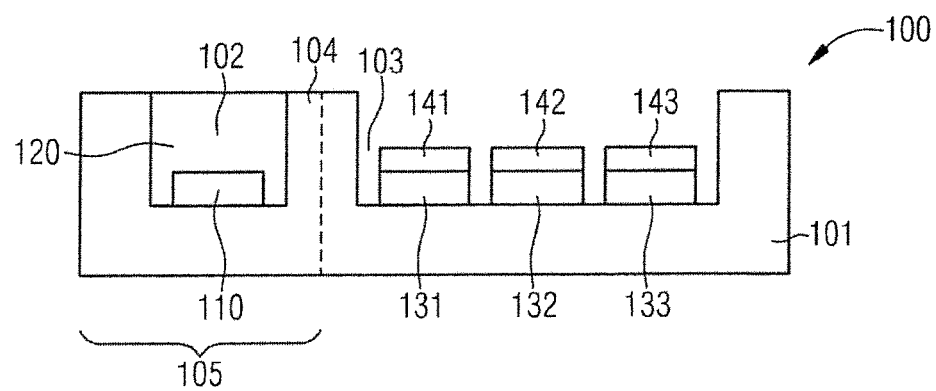
FIG. 3 schematically shows an optical sensor with a semiconductor chip, a conversion phosphor, and three light detectors.

FIG. 3 shows a further cross section through an optical sensor 100 which substantially corresponds to the optical sensor of FIG. 1. In this case, the first recess 102 of the housing 101 is filled with a conversion phosphor 120. This conversion phosphor 120 converts the light of the semiconductor chip 110 having an emission wavelength of less than 570 nanometers into green light of the first wavelength range, red light of the second wavelength range and infrared radiation of the third wavelength range. Thus, the conversion phosphor 120 is configured to absorb the light of the semiconductor chip 110 and emit electromagnetic radiation in the three wavelength ranges. The conversion phosphor 120 has a matrix material with three different, narrowband phosphors, wherein the emission wavelengths of the phosphors lie within the three wavelength ranges. The phosphors may each have a phosphor whose converted light has a narrow bandwidth.

Thus, the optical sensors 100 in FIGS. 1 to 3 respectively differ in the region of the light source 105. The second recess 103 and the light detectors and filters situated therein are identical for all three optical sensors of FIGS. 1 to 3.

Figure 4:
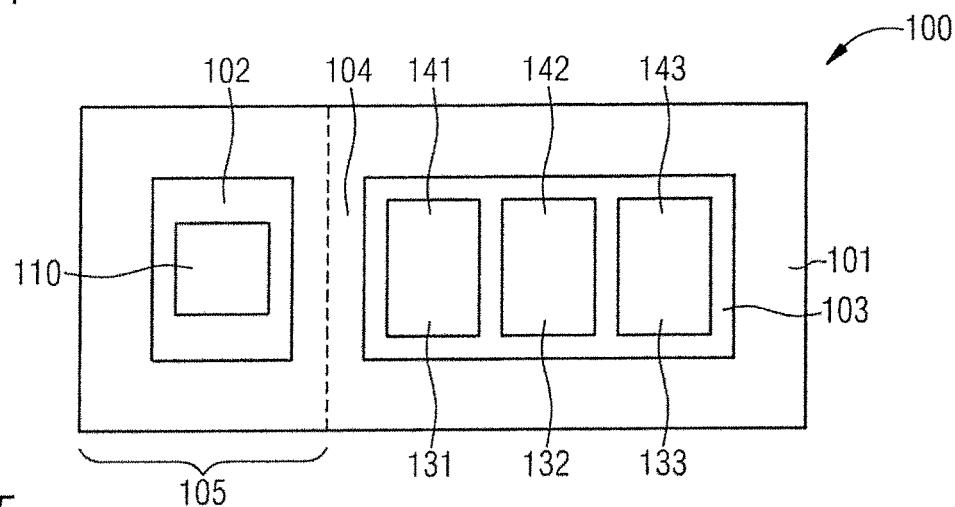
FIGS. 4 to 6 schematically show different arrangement options for the three light detectors.

FIG. 4 shows an optical sensor 100 in a plan view. A housing 101 has a first recess 102 and a second recess 103. The two recesses 102, 103 are separated from one another by a web 104. A semiconductor chip 110 is arranged in the first recess 102. The first recess 102 with the semiconductor chip 110 and the adjoining parts of the house at 101 once again forms the light source 105. The light source 105 can be configured in an analogous manner to one of the light sources 105 of FIGS. 1 to 3. Three light detectors are situated in the second recess 103, with a first light detector 131 having the smallest distance from the light source 105, a second light detector 132 having a greater distance from the light source 105 than the first light detector 131, and a third light detector 133 having the greatest distance from the light source 105. A first filter 141 is arranged on the first light detector 131. A second filter 142 is arranged on the second light detector 132. A third filter 143 is arranged on the third light detector 133. The first filter 141 transmits green light of a first wavelength range. The second filter 142 transmits red light of a second wavelength range and the third filter 143 transmits infrared radiation of a third wavelength range. The filters 141, 142, 143 are non-transmissive for the respective other wavelength ranges. Thus, infrared radiation is detected furthest away from the light source and the green light is detected closest to the light source.

Figure 5:
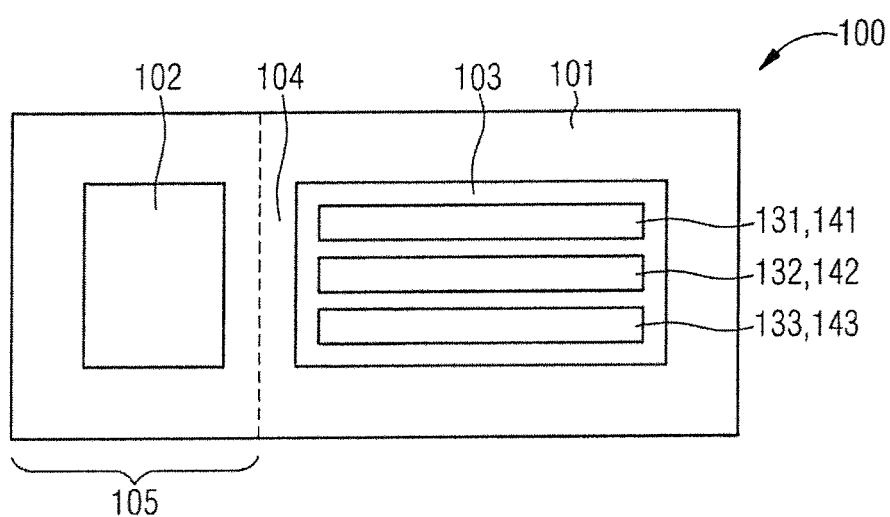

FIG. 5 shows a plan view of a further example of an optical sensor 100. A housing 101 likewise has a first recess 102 and a second recess 103. One of the light sources 105 of FIGS. 1 to 3 can once again be arranged within the first recess 102. Once again, three light detectors 131, 132, 133 with three associated filters 141, 142, 143 are arranged in the second recess 103, wherein light detectors 131, 132, 133 and filters 141, 142, 143 have the same properties as in FIG. 4. The light detectors 131, 132, 133 and filters 141, 142, 143 have an elongate form and are arranged in the second recess 103 such that they each have the same distance from the light source 105. Compared to FIG. 4, the light detectors 131, 132, 133 and filters 141, 142, 143 are arranged with a 90 degrees rotation.

Figure 6:
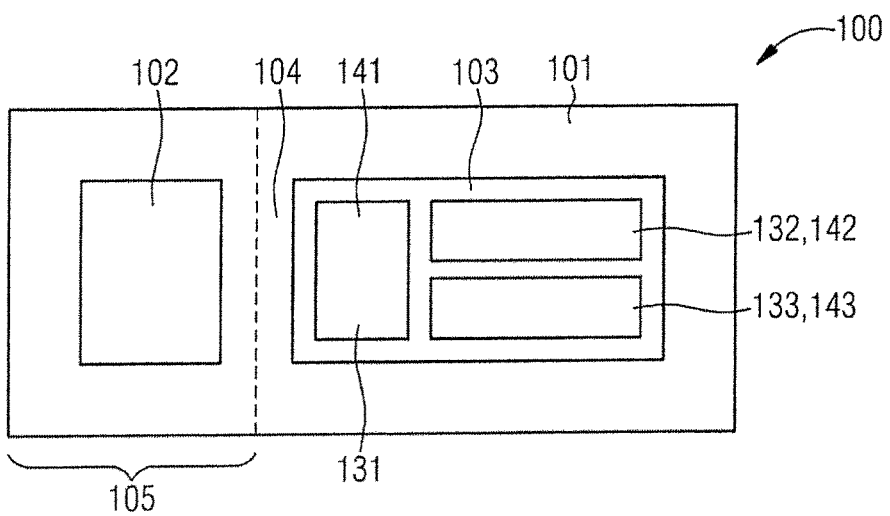

FIG. 6 shows a further example of an optical sensor 100 in the plan view. A housing 101 once again has a first recess 102 and a second recess 103. Arranged within the first recess 102, there is a light source 105, which is analogous to one of the light sources 105 of FIGS. 1 to 3. Once again, three light detectors 131, 132, 133 with associated filters 141, 142, 143 are arranged in the second recess 103. The first light detector 131 with the first filter 141 is arranged on the side of the second recess 103 facing the light source 105. The second light detector 132 and the third light detector 133 with the associated filters 142, 143 are arranged with a 90 degrees rotation in relation to the first light detector 131, and so the distance of the second light detector 132 and of the third light detector 133 from the light source is the same, but greater than the distance of the first light detector 131 from the light source 105. The light detectors 131, 132, 133 and the filters 141, 142, 143 in this case correspond to the light detectors and filters of FIGS. 1 to 5.

Figure 7:
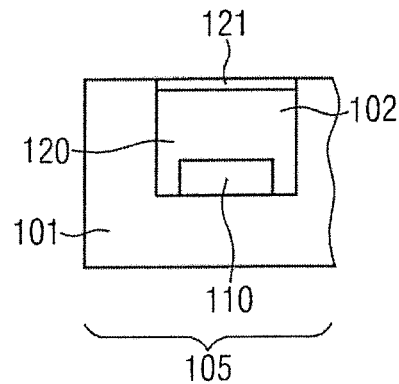
FIGS. 7 to 9 schematically show various examples of the light source with a conversion phosphor.

FIG. 7 shows a cross section through a further light source 105 suitable as a part of the optical sensor 100. The light source of FIG. 7 corresponds substantially to the light source in FIG. 3. A housing 101 has a first recess 102, in which a semiconductor chip 110 with an emission wavelength of less than 570 nanometers is arranged. The first recess 102 is filled with a conversion phosphor 120, with the conversion phosphor 120 corresponding to the conversion phosphor of FIG. 3. A protective layer 121 is arranged above the conversion phosphor 120, the protective layer sealing the first recess 102 and the conversion phosphor 120 such that environmental influences are not able to act on the conversion phosphor 120.

Figure 8:
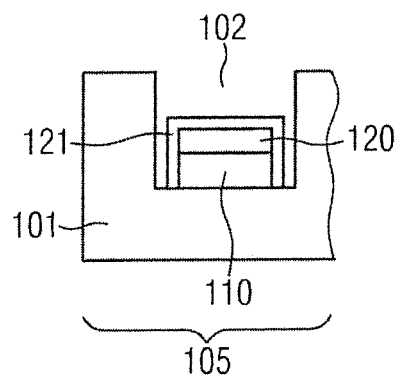

FIG. 8 shows a further example of a light source 105 for an optical sensor. A semiconductor chip 110 having an emission wavelength of less than 570 nanometers is arranged in a first recess 102 of a housing 101. A conversion phosphor 120 is arranged in the form of a plate directly on the semiconductor chip 110. The semiconductor chip 110 and conversion phosphor 120 are encapsulated by a protective layer 121. The conversion phosphor 120 once again corresponds to the conversion phosphor of FIG. 7.

Figure 9:
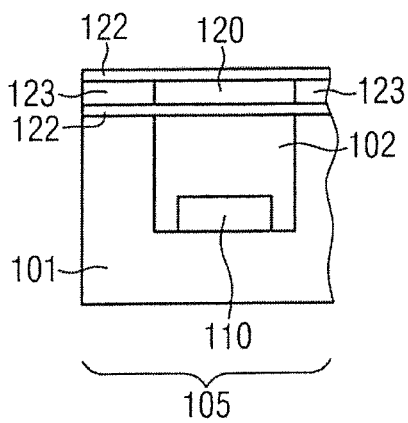

FIG. 9 shows a further example of a light source 105. Arranged in a first recess 102 of a housing 101, there is a semiconductor chip 110, with the semiconductor chip 110 having an emission wavelength of less than 570 nanometers. The first recess 102 is covered by a glass plate 122. A spacer 123 is mounted on the glass plate 122 and situated above the glass plate 122. A further glass plate 122 is situated above the spacer 123. The spacer 123 and the two glass plates 122 form a cavity here, the conversion phosphor 120 being introduced therein. The conversion phosphor 120 is sealed from the surroundings by the two glass plates 122 and the spacer 123, i.e., it is arranged within the space defined by the two glass plates 122 and the spacer 123.

The three light sources 105 of FIGS. 7 to 9 can each be combined with the three arrangements of the filters 131, 132, 133 of FIGS. 4 to 6.

The conversion phosphor 120 may have quantum dots. Quantum dots are particularly suitable as conversion phosphors since they have a narrowband emission characteristic. In this case, narrowband means that the full width at half maximum of the emission peak is 30 to 40 nanometers. Here, the green light of the first wavelength range has a maximum intensity at a wavelength of 570 nanometers. The red light of the second wavelength range has a maximum intensity at 660 nanometers and the infrared radiation has a maximum wavelength greater than 800 nanometers. By way of the quantum dots and the conversion phosphor with a small full width at half maximum arising as a result thereof, it is possible for the green light, the red light and the infrared radiation to have three separate peaks and not to overlap.

A filter 141, 142, 143 may be an interference filter. Interference filters consist of different layers with different refractive indices. By way of a suitable selection of the layer thicknesses and refractive indices of the layers, it is possible to produce a filter which has a steep flank at a specific wavelength. This means that a filter which transmits more than 90% at a first wavelength is non-transmissive for the light of a second wavelength at a second wavelength that only differs from the first wavelength by a few nanometers, in particular by less than 10 nanometers.

The combination of a conversion phosphor 120 consisting of quantum dots and filters 141, 142, 143 configured as interference filters yields a particularly advantageous example of the optical sensor 100.

The green light may have a wavelength of 530 to 610 nanometers, with the maximum intensity possibly lying at 670 nanometers. The red light may have a wavelength of 620 to 700 nanometers, with the maximum intensity possibly lying at 660 nanometers. The infrared radiation may have a wavelength of greater than 800 nanometers. An optical sensor with the aforementioned wavelength ranges for the green light, the red light and the infrared radiation is achievable with quantum dots as conversion phosphor 120 and with interference filters as filters 141, 142, 143.

FIGS. 1 to 9 do not show any connectors of the semiconductor chips 110, 111, 112, 113 or of the light detectors 131, 132, 133. These can be provided within the housing 101 according to the prior art by a person skilled in the art.

Figure 10:
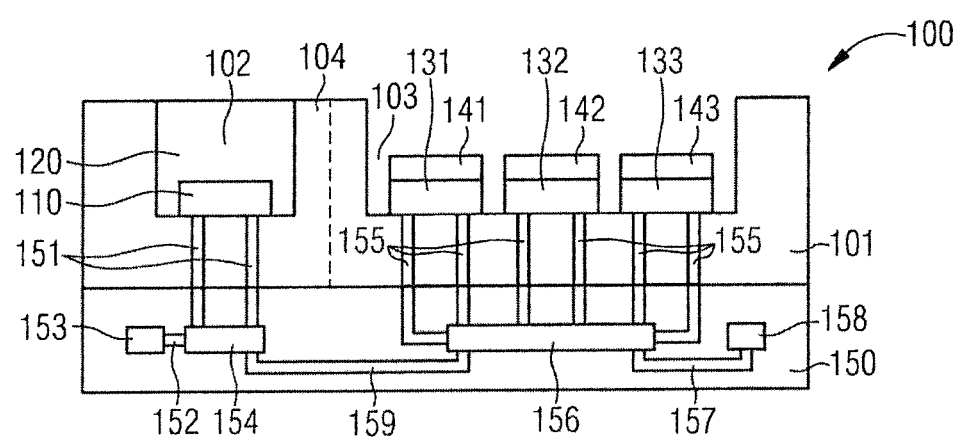
FIG. 10 schematically shows an optical sensor with an electronic circuit.

FIG. 10 shows a cross section through a further example of an optical sensor 100, with the optical sensor 100 substantially corresponding to the optical sensor 100 of FIG. 3. An electronic circuit 150 is arranged below the housing 101. The electronic circuit 150 is configured to supply the semiconductor chip 110 with voltage and undertake the evaluation of the signals of the three light detectors 131, 132, 133. To this end, the electronic circuit 150 has a controller for a semiconductor chip 154 connected to the semiconductor chip 110 by electric lines 151. The electronic circuit 150 moreover has a connector for a voltage supply 153 connected to the controller for the semiconductor chip 154 with an electric line 152. Moreover, the electronic circuit 150 has evaluation electronics 156 connected to the three light detectors 131, 132, 133 by electric lines 155. The evaluation electronics 156 connect to a data interface 158 by way of a data line 157. FIG. 10 likewise shows, even though this is only optional, a data line between the controller 154 for the semiconductor chip and the evaluation electronics 156. Thus, the optical sensor 100 has a voltage supply 153 and a data interface 158 as connectors to the outside, and it is otherwise controlled by the electronic circuit 150.

The controller 154 may be configured to operate the semiconductor chip 110 in a pulsed manner. The evaluation electronics 156 are configured to receive information about the pulses via the data line 159 and to take this into account when evaluating the signals of the light detectors 131, 132, 133.

Even though our optical sensors are illustrated in more detail and described in detail by preferred examples, this disclosure is not limited by the examples and other variations can be derived herefrom by those skilled in the art without departing from the scope of protection of the appended claims.

The application claims priority of DE 10 2015 117 940.7, the subject matter of which is incorporated herein by reference.

The invention claimed is:

1. An optical sensor that captures a heart rate and/or a blood oxygen content, comprising:
    a light source comprising at least one light-emitting semiconductor chip and emits electromagnetic radiation with three different wavelength ranges, wherein a first wavelength range comprises green light, a second wavelength range comprises red light and a third wavelength range comprises infrared radiation, and three light detectors, wherein the three light detectors each comprise a filter for electromagnetic radiation, wherein a first filter is transmissive for light of the first wavelength range and non-transmissive for light of the second wavelength range and the infrared radiation of the third wavelength range, a second filter is transmissive for light of the second wavelength range and non-transmissive for light of the first wavelength range and the infrared radiation of the third wavelength range and a third filter is transmissive for the infrared radiation of the third wavelength range and non-transmissive for light of the first and the second wavelength range, wherein the light-emitting semiconductor chip has an emission wavelength of less than 570 nanometers and the light source comprises a conversion phosphor, the conversion phosphor converts the light of the semiconductor chip into electromagnetic radiation with the first wavelength range, the second wavelength range and the third wavelength range, the conversion phosphor comprises a matrix material with three different narrowband phosphors, and the emission wavelengths of the phosphors lie within the three wavelength ranges.

2. The optical sensor according to claim 1, wherein the conversion phosphor comprises quantum dots.

3. The optical sensor according to claim 2, wherein the conversion phosphor comprises cadmium selenide quantum dots with a diameter of 3.0 to 3.5 nanometers or indium phosphide quantum dots with a diameter of 1.8 to 2.2 nanometers, the conversion phosphor additionally comprises cadmium selenide quantum dots with a diameter of 7.5 to 8.5 nanometers or indium phosphide quantum dots with a diameter of 2.8 to 3.2 nanometers, and the conversion phosphor comprises indium arsenide quantum dots with a diameter of 3.0 to 6.0 nanometers or lead selenide quantum dots with a diameter of greater than 5.0 nanometers or copper indium phosphide quantum dots with a diameter of 2.5 to 5.8 nanometers.

4. The optical sensor according to claim 2, wherein the conversion phosphor comprises cadmium selenide quantum dots with a diameter of 3.0 to 3.5 nanometers to produce the green light of the first wavelength range.

5. The optical sensor according to claim 2, wherein the conversion phosphor comprises indium phosphide quantum dots with a diameter of 1.8 to 2.2 nanometers to produce the green light of the first wavelength range.

6. The optical sensor according to claim 2, wherein the conversion phosphor comprises cadmium selenide quantum dots with a diameter of 7.5 to 8.5 nanometers to produce the red light of the second wavelength range.

7. The optical sensor according to claim 2, wherein the conversion phosphor comprises indium phosphide quantum dots with a diameter of 2.8 to 3.2 nanometers to produce the green light of the first wavelength range.

8. The optical sensor according to claim 2, wherein the conversion phosphor comprises indium arsenide quantum dots with a diameter of 3.0 to 6.0 nanometers to produce the infrared radiation of the third wavelength range.

9. The optical sensor according to claim 2, wherein the conversion phosphor comprises lead selenide quantum dots with a diameter of greater than 5.0 nanometers to produce the infrared radiation of the third wavelength range.

10. The optical sensor according to claim 2, wherein the conversion phosphor comprises copper indium phosphide quantum dots with a diameter of 2.5 to 5.8 nanometers to produce the infrared radiation of the third wavelength range.

11. The optical sensor according to claim 1, wherein at least one filter is an interference filter.

12. The optical sensor according to claim 1, wherein the green light has a wavelength of 530 to 610 nanometers, the red light has a wavelength of 620 to 700 nanometers and the infrared radiation has a wavelength of greater than 800 nanometers.

13. The optical sensor according to claim 1, having an electronic circuit configured to evaluate signals from the light detectors and to supply the light source with power.

14. The optical sensor according to claim 13, wherein the power supply of the light source can be operated in a pulsed manner and the circuit to evaluate the signals from the light detectors is configured to take account of the pulses.

* * * * *